US009273992B2

(12) United States Patent
Lindstrom (10) Patent No.: US 9,273,992 B2
(45) Date of Patent: Mar. 1, 2016

(54) RADIATION FORCE BALANCE CALIBRATOR

(75) Inventor: Matti Olavi Lindstrom, Espoo (FI)

(73) Assignee: Koninklijke Philips N.V., Eindhoven (NL)

( * ) Notice: Subject to any disclaimer, the term of this patent is extended or adjusted under 35 U.S.C. 154(b) by 331 days.

(21) Appl. No.: 13/877,408

(22) PCT Filed: Sep. 28, 2011

(86) PCT No.: PCT/IB2011/054266
§ 371 (c)(1),
(2), (4) Date: Apr. 2, 2013

(87) PCT Pub. No.: WO2012/046164
PCT Pub. Date: Apr. 12, 2012

(65) Prior Publication Data
US 2013/0197350 A1  Aug. 1, 2013

(30) Foreign Application Priority Data

Oct. 4, 2010  (EP) ..................... 10186359

(51) Int. Cl.
| | |
|---|---|
| A61B 5/05 | (2006.01) |
| G01H 11/00 | (2006.01) |
| G01H 3/00 | (2006.01) |
| A61B 8/00 | (2006.01) |
| A61B 5/055 | (2006.01) |
| A61B 19/00 | (2006.01) |
| A61N 7/02 | (2006.01) |

(52) U.S. Cl.
CPC ............... *G01H 11/00* (2013.01); *A61B 8/587* (2013.01); *G01H 3/005* (2013.01); *A61B 5/055* (2013.01); *A61B 2019/5236* (2013.01); *A61N 7/02* (2013.01)

(58) Field of Classification Search
None
See application file for complete search history.

(56) References Cited

U.S. PATENT DOCUMENTS

| | | |
|---|---|---|
| 3,915,017 A | 10/1975 | Robinson |
| 6,978,677 B2 | 12/2005 | Bajram |

(Continued)

FOREIGN PATENT DOCUMENTS

| | | |
|---|---|---|
| WO | 2007025437 A1 | 3/2007 |
| WO | 2009066805 A1 | 5/2009 |

OTHER PUBLICATIONS

Kikuchi et al., "Ultrasonic Power Measurements by Radiation Force Balance Method", Jpn J Appl Phys, vol. 39, 2000.*

(Continued)

*Primary Examiner* — Christopher Cook (57) ABSTRACT

A radiation force balance calibrator (100) for calibrating a high intensity focused ultrasound transducer (106), the radiation force balance calibrator comprising: a balance frame (130); a force sensor (138) for measuring force, wherein the force sensor is attached to the balance frame; a balance (124) with first (132) and second ends (134), wherein the first end is attached to a pivot (128) for enabling the balance to pivot relative to the balance frame, wherein the second end is adapted for exerting force onto the force sensor; an oil target phantom (116) connected to the balance for absorbing ultrasound radiation (112, 114) from the high intensity focused ultrasound transducer, wherein the absorption of ultrasonic radiation causes a reduction in the force exerted by the balance on the force sensor; and wherein the radiation force balance calibrator is constructed of non-magnetic materials.

20 Claims, 9 Drawing Sheets

(56) References Cited

U.S. PATENT DOCUMENTS

2007/0204671 A1* 9/2007 Sliwa et al. .................. 73/1.83
2010/0036292 A1 2/2010 Darlington et al.

OTHER PUBLICATIONS

Li et al., "MRI Compatible Robot Systems for Medical Intervention", Apr. 2010.*

Beccai et al., "Design and Fabrication of a Hybrid Silicon Three-Axial Force Sensor for Biomechanical Applications", available online Feb. 5, 2005.*

Howard, S., et al.; A Novel Device for Total Acoustic Output Measurement of High Power Transducers; 2010; 9th International Symposium on Therapeutic Ultrasound; vol. 1215; pp. 341-344.

Johns, L. D., et al.; Analysis of Effective Radiating Area, Power, Intensity, and Field Characteristics of Ultrasound Transducers; 2007; Arch Phys Med Rehabil; 88(1)124-129.

Qian, Z. W., et al.; Acoustic Radiation Force on Object and Power Measurements of Focusing Source (HIFU); 2008; IEEE International Ultrasonics Symposium Proceedings; 2008.0440:1793-1796.

Shaw, A.; A Buoyancy Method for the Measurement of Total Ultrasound Power Generated by HIFU Transducers; 2008; Ultrasound in Med. & Biol.; 34(8)1327-1342.

Sutton, Y., et al.; An ultrasound mini-balance for measurement of therapy level ultrasound; 2006; Phys Med. Biol; 51:3397-3404.

* cited by examiner

RADIATION FORCE BALANCE CALIBRATOR

TECHNICAL FIELD

The invention relates to the calibration of high intensity focused ultrasound systems, in particular to a magnetic resonance imaging system compatible calibrator.

BACKGROUND OF THE INVENTION

MRI-guided HIFU therapy devices are sometimes calibrated by service engineers on the field. One major calibration factor is the ultrasonic power output at different settings of the device. Calibration may be called for e.g. in case some components in the electrical chain of ultrasound (US) generation are changed, the transducer itself is replaced, or the built-in QA self-test indicates a discrepancy.

The gold standard measurement of ultrasound power output is the radiation force balance (RFB) method. This is the test performed in factory calibration of the device, using an accurate and sensitive laboratory balance. However, once the therapy device is installed, the cabling will not allow the therapy bed (and its ultrasound output window) to reach very far from the MR device and its stray B0 field. Laboratory balances rely on a magnetic feedback balancing method, and are unsuitable for measurement in these conditions. A radiation force method is known from the paper '*A buoyancy method for the measurement of total ultrasound power generated by HIFU transducers*' by A. Shaw in Ultrasound in Med. and Biol 34 (2008)1327-1342. This known method relies on the principle that a due to reflection or absorption of travelling ultrasound waves on a target, a force is exerted on the target equal to the change in momentum flux associated with the wave.

SUMMARY OF THE INVENTION

The invention provides for a radiation force balance calibrator, an ultrasonic apparatus, a computer program product, and a computer-implemented method in the independent claims. Embodiments are given in the dependent claims.

There is therefore a need for an improved radiation force balance calibrator. Embodiments of the invention may solve this problem and others by constructing a radiation force balance calibrator from magnetic field compatible materials. Additionally a force sensor which is able to function in the magnetic field of a magnetic resonance imaging system are used in some embodiments.

In a hospital or other healthcare providing location, there may be a large number of vibration sources that can interfere with the proper function of a radiation force balance calibrator. However it is noted that over the time frame of a calibration the spectral content of the vibrational noise is constant enough to be average out. To achieve this averaging measurements from the radiation force balance calibrator are compared to simulations which model the response for given intensity of ultrasound radiation.

Several indirect methods for Ultra Sound (US) output power calibration exist, e.g. Magnetic resonance (MR) imaging of heating in a phantom, or more recently, applied radiation force push quantification by displacement imaging. None of these exhibit the direct traceable calibration ability of RFB measurement. This invention describes a field-deployable RFB calibration system that uses MR stray field tolerant mechanics and electronics for direct calibration of an installed system. The radiation force is measured with a resistive force sensor bridge, amplified, digitized and processed to yield a power calibration result.

Particular embodiments may have the following advantages or features:
Calibration can be done with the therapy device in the magnet room
  This ensures that all individual therapy system components are the same ones used in therapy and are installed in exactly the same configuration as used for therapy.
  Extra effort of reconfiguring the system for calibration is avoided
A robust oil-filled absorbing target is used
  Enables measurements of very high (>400 W) acoustic powers directly
Includes a primary calibration with traceable calibration weights every time
  Each individual measurement has calibration data included
Uses functional fitting to extract data from the noisy force sensor trace
  Knowledge about the excitation function (power levels driven from the therapy system) is put to optimal use
  Algorithm uses both radiation force and buoyancy change as inputs
  Deals effectively with vibrational noise from environment and intrinsic noise from the sensor.

A computer-readable storage medium as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM) memory, Read Only Memory (ROM) memory, an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

Computer memory is an example of a computer-readable storage medium. Computer memory is any memory which is directly accessible to a processor. Examples of computer memory include, but are not limited to: RAM memory, registers, and register files.

Computer storage is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A computing device as used herein refers to any device comprising a processor. A processor is an electronic component which is able to execute a program or machine executable instruction. References to the computing device comprising "a processor" should be interpreted as possibly containing more than one processor. The term computing device should also be interpreted to possibly refer to a collection or network of computing devices each comprising a processor. Many programs have their instructions performed by multiple processors that may be within the same computing device or which may even distributed across multiple computing device.

'Human interface hardware' as used herein is an interface which allows a user or operator to interact with a computer or computer system. Human interface hardware may provide information or data to the operator and/or receive information or data from the operator. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of receiving information or data from an operator.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for a radiation force balance calibrator for calibrating a high intensity focused ultrasound transducer. The radiation force balance calibrator comprises a balance frame. The balance frame is a frame or mounting plate or holder for holding the components of the radiation force balance calibrator. The radiation force balance calibrator further comprises a force sensor for measuring force. The force sensor is attached to the balance frame. The radiation force balance calibrator further comprises a balance with first and second ends. The first end is attached to a pivot for enabling the balance to pivot relative to the balance frame. The second end is adapted for exerting force onto the force sensor. The radiation force balance calibrator further comprises an oil target phantom connected to the balance for absorbing ultrasound radiation from the high intensity focused ultrasound transducer. The absorption of ultrasonic radiation causes a reduction in the force exerted by the balance on the force sensor. The radiation force balance calibrator is constructed of non-magnetic materials. In other words the radiation force balance calibrator is compatible with being placed into a region of a high magnetic field such as the magnetic field generated by a magnetic resonance imaging system. According to the invention wherein the radiation further comprises a processor (422) and a memory (426, 428), wherein the memory contains instructions (446, 448, 450, 452, 454) for execution by the processor, wherein execution of the instructions cause the processor to perform the steps of:

i. computing an estimate force on the phantom due to absorbing ultrasound radiation (112, 114) from the high intensity focused ultrasound transducer on the basis of activation signals to activate the high intensity focused ultrasound transducer (106) to emit ultrasound radiation and model parameters that are descriptive for the relationship between the activation signals and the output power of the transducer and the transfer of the output power to the force exerted by the balance on the force sensor, ii. activate the high intensity focused ultrasound transducer and measure the force exerted by the balance on the force sensor, iii. compute the difference between the measured force and the estimated force iv. update the model parameters on the basis of the computed difference and iterate steps i. through iv. until the difference is less than a pre-determined threshold. This embodiment is particularly advantageous because this radiation force balance calibrator may be used for calibrating a high intensity focused ultrasound transducer that is integrated into a magnetic resonance imaging system. The radiation force balance calibrator enables accurate calibration while the ultrasonic apparatus remains mounted within the magnetic resonance imaging system. Notably, force sensors that are compatible with the magnetic resonance environment can be used. Such MR compatible force sensors, such a micro-machined silicon bridge sensors usually have a lower signal-to-noise ratio as compared to force sensors conventionally employed in the known radiation force method. Further, in the neighbourhood of the magnetic resonance imaging system, usually there are several sources of noise, such as due to people passing by near the room where the magnetic resonance imaging system with the ultrasound apparatus is set up. These perturbations are compensated for in the radiation force balance calibrator of the invention, by extracting the proper parameter values for a physical model of the transfer of the activation signals into output power from the transducers and subsequent transfer to force on the target. Fitting these parameters compensates for the lower signal-to-noise of the force measured by the force sensor.

In another embodiment the radiation force balance calibrator further comprises a basin for holding water and the oil target phantom. The balance pivots above the basin. The basin is adapted for attaching above an ultrasound window in a patient support. Essentially the oil target phantom is suspended in a water bath within the basin. When the ultrasound radiation is absorbed by the oil target phantom the ultrasonic radiation exerts a force which lifts the oil target phantom and results in a reduction of the force measured by the force sensor. Additionally the oil target phantom may be heated by the ultrasonic radiation. This causes a change in the buoyancy of the oil target phantom. As the oil target phantom is heated it becomes lighter relative to the water and also due to this effect the force exerted on the force sensor by the balance is reduced.

In another embodiment the radiation force balance calibrator further comprises a calibration weight holder attached to the second end. This embodiment is advantageous because calibration weights may be placed which cause the balance to exert a force on the force sensor. This may be useful for calibrating the radiation force balance calibrator during use.

In another embodiment the radiation further comprises a processor and a memory. The memory contains instructions for execution by the processor. Execution of the instructions causes the processor to perform the step of measuring a first dataset with the force sensor. At least a portion of the first dataset is acquired with a calibration weight in the calibration weight holder. Execution of the instructions causes the processor to further perform the step of measuring a second dataset with the force sensor with the calibration weight in the calibration weight holder. The second dataset is measured after the first dataset. At least some of the second dataset is measured when the oil target phantom is absorbing ultrasonic radiation. Execution of the instructions further causes the processor to perform the step of measuring a third dataset with the force sensor. At least a portion of the third dataset is acquired with a calibration weight in the calibration weight holder. The third dataset is measured after the second dataset.

Execution of the instructions further cause the processor to perform the step of calculating the calibration for the high intensity focused ultrasound transducer in accordance with the first dataset, the second dataset, and the third dataset. This embodiment is advantageous because data has been acquired in the first dataset using a calibration weight for part of the measurements; the second dataset has been acquired using a weight in the calibration weight holder and with ultrasound radiation absorbed by the oil target phantom. The third dataset was acquired again with at least a calibration weight in the weight holder. The first dataset and the third dataset are not necessarily acquired with ultrasound energy being directed at the oil target phantom. The combination of these three datasets allows the calibration of the high intensity focused ultrasound transducer. In more detail, the first dataset is measured in that an initial subset of data is recorded with no calibration weight in the calibration weight holder, then a first weight is placed in the calibration weight holder and a subsequent subset of data is recorded. Additionally, further weights may be placed in the calibration weight holder and further subsequent datasets recorded for each further weights added to the calibration weight holder. These initial and subsequent recorded datasets together form the first dataset. During recording to these initial and subsequent datasets, preferably no ultrasound radiation is radiated onto the phantom. Then, the second dataset is measured when the phantom is absorbing ultrasonic radiation. After that, a following subset of data is recorded while the further weights are still in the calibration weight holder. Further following subsets of data are recorded, after having removed one or more of the weights from the calibration weight holder. Finally, a final subset of data is recorded with all weights removed from the calibration weight holder. These following subsets and final subset of data together form the third dataset. Comparison of the first and third datasets allows to verify the consistency and stability of the radiation force balance calibrator. Notably, changes of the buoyancy properties of the phantom due to the absorption of ultrasonic radiation can be corrected for. In practice, apart from these temporal variations of the buoyancy, the radiation force balance calibrator is quite stable and has a high consistency between the first and third datasets. It is understood herein that references to a processor and a memory may actually refer to multiple processors or multiple memories. For instance a single computer system may have multiple processors or alternatively a network or collection of computers may be used collectively to perform the method.

In another embodiment at least some of the second dataset is measured when the oil target phantom is absorbing ultrasonic radiation of at least two different intensities. The instructions further cause the processor to perform the step of receiving ultrasonic pulse timing data descriptive of ultrasonic radiation emitted by the high intensity focused ultrasound transducer during the measurement of the second dataset. The calibration is calculated in accordance with the ultrasonic pulse timing data. Essentially the ultrasonic pulse timing data is data which describes the power or intensity settings used for driving the high intensity focused ultrasound transducer. The pulse timing data may in some circumstances be considered to be an expected power output by the high intensity focused ultrasound transducer. It is advantageous to use two different intensities along with the pulse timing data because this may be used in conjunction with a model to calibrate the high intensity focused ultrasound transducer.

In another embodiment the step of calibrating a calibration comprises modeling an expected second dataset in accordance with the ultrasonic pulse timing data. The ultrasonic pulse timing data is descriptive of an intended intensity of ultrasonic radiation that is emitted by the high intensity focused ultrasound transducer. The step of calculating the calibration further comprises calculating a residual between the expected second dataset and the second dataset. The modeling and the calculation of the residual are repeated iteratively until the model converts to the calibration.

In another embodiment the modeling is performed using a finite difference model for simulating radiation force of ultrasonic radiation on the oil target phantom. The finite difference model is used to simulate the mechanical force which the ultrasound radiation exerts on the oil target phantom.

In another embodiment the finite difference model is adapted for simulating the buoyancy of the oil target phantom by calculating the heat transfer due to the absorption of ultrasonic radiation within the oil target phantom and heat exchange with its surroundings. The oil target phantom is suspended in a water bath. By modeling the heating of the oil target phantom and the loss of heat with the surrounding water bath the change in the buoyancy of the oil target phantom can be calculated.

In another embodiment the functioning of the force sensor is not affected by a magnetic field with a strength under 20 T. This embodiment is advantageous because the force sensor functions within a magnetic field.

In some embodiments the force sensor is placed within the main field or imaging zone of the magnet.

In other embodiments, the high intensity focused ultrasound transducer is moved to the fringe field region of the magnet during calibration of the high intensity focused ultrasound transducer.

In some embodiments the electronics for operating the force sensor are located in the fringe field of the magnet. In a magnetic resonance imaging system the imaging region of a magnet may have a magnetic field of the order of several Tesla, such as 1.5 Tesla or 3 Tesla. Outside of the magnet, the fringe field of the magnetic may drop rapidly. For instance for a 1.5 Tesla or 3 Tesla magnet the fringe field may be on the order of 100 mTesla. The electronics could be placed in the fringe field by using long twisted pair leads going to the force sensor.

In another embodiment the strain sensor is a micro-machined silicon bridge sensor. The use of this type of sensor is advantageous because these micro-machined silicon bridge sensors are able to function within a high magnetic field such as those used for magnetic resonance imaging.

In another aspect the invention provides for an ultrasonic apparatus comprising a patient support for supporting a patient and an ultrasound transducer system. The ultrasound transducer system is mounted below an ultrasound window in the patient support. The ultrasound apparatus further comprises a radiation force balance calibrator according to an embodiment of the invention. The radiation force balance calibrator is mounted above the ultrasound window. This is advantageous because the radiation force balance calibrator may be used to calibrate the ultrasound transducer after it has been installed at a hospital or other healthcare facility. Normally this is performed in a specialized calibration laboratory.

In another embodiment the ultrasound system further comprises a magnetic resonance imaging system. The magnetic resonance imaging system comprises a magnet adapted for generating the magnetic field for orienting the magnetic spins of nuclei of a subject located within an imaging volume. The magnetic resonance imaging system further comprises a radio frequency transceiver. The radio frequency transceiver is adapted for connecting to a radio frequency coil for acquiring magnetic resonance data from the imaging volume. It is understood herein that the radio frequency transceiver may also refer to individual radio frequency transmitters and receivers. Likewise individual transmit and receive radio frequency coils may also be used. It is also understood that the magnetic resonance data is primarily from the imaging volume. However, Fourier techniques are used to reconstruct the images and magnetic spins outside of the imaging volume may contribute to the construction of the image. The magnetic resonance imaging system further comprises a magnetic field gradient coil for spatial encoding of the magnetic spins of nuclei within the imaging volume. It is understood herein that a magnetic field gradient coil refers to the set of magnetic field gradient coils. Typically there are three separate sets of magnetic field gradient coils for each of the spatial directions.

The magnetic resonance imaging system further comprises a computer system for controlling the operation of the magnetic resonance imaging system and the ultrasound transducer system. The computer system is adapted for controlling the ultrasound transducer system in accordance with the magnetic resonance data. In other words the computer system is adapted such that the images generated by the magnetic resonance imaging may be used for guiding the use of the ultrasound transducer system.

In another aspect the invention provides for a computer program product comprising machine-executable instructions for execution by a processor of a radiation force balance calibrator according to an embodiment of the invention. Execution of the instructions causes the processor to perform the step of measuring a first dataset with the force sensor. A portion of the first dataset is acquired with a calibration weight in the calibration weight holder. Execution of the instructions further cause the processor to perform the step of measuring a second dataset with the force sensor with a calibration weight in the calibration weight holder. The second dataset is measured after the first dataset. The second dataset is measured when the oil target phantom is absorbing ultrasonic radiation. Execution of the instructions further causes the processor to perform the step of measuring a third dataset with the force sensor. At least a portion of the third dataset is acquired with a calibration weight in the calibration weight holder. The third data set is measured after the second data set. Execution of the instructions further causes the processor to perform the step of calculating the calibration for the high intensity focused ultrasound transducer in accordance with the first data set, the second data set, and the third data set.

In another aspect the invention provides for a computer-implemented method of calibrating a high intensity focused ultrasound transducer using a radiation force balance calibrator according to an embodiment of the invention. The method comprises measuring a first dataset with the force sensor. At least a portion of the first dataset is acquired with a calibration weight in the calibration weight holder. The method further comprises measuring a second dataset with the force sensor with a calibration weight in the calibration weight holder. The second dataset is measured after the first dataset. The second dataset is measured when the oil target phantom is absorbing ultrasonic radiation. The method further comprises measuring a third dataset with the force sensor. At least a portion of the third dataset is acquired with a calibration weight in the calibration weight holder. The third dataset is measured after the second dataset. The method further comprises calculating a calibration for the high intensity focused ultrasound transducer in accordance with the first dataset, the second dataset, and the third dataset.

BRIEF DESCRIPTION OF THE DRAWINGS

In the following preferred embodiments of the invention will be described, by way of example only, and with reference to the drawings in which:

FIG. 5b shows a side view of the radiation force balance calibrator shown in FIG. 5a;

FIG. 5c shows a top view of the radiation force balance calibrator shown in FIG. 5a;

FIG. 6b shows a side view of the radiation force balance calibrator of FIG. 6a;

FIG. 6C shows an exploded parts view of the radiation force balance calibrator of FIG. 6a.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
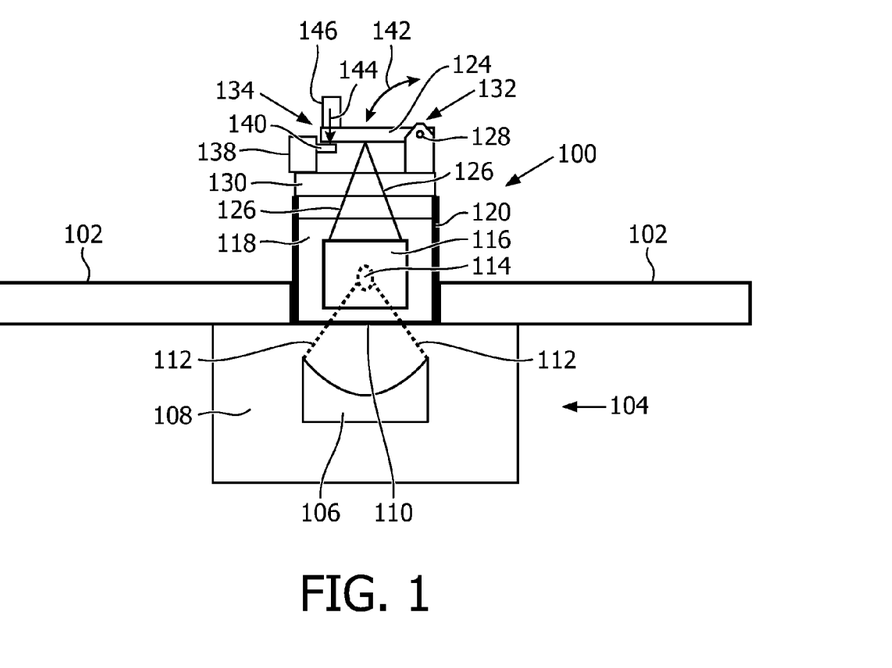
FIG. 1 illustrates a radiation force balance calibrator according to an embodiment of the invention.

FIG. 1 shows a diagram which illustrates a radiation force balance calibrator 100 according to an embodiment of the invention. The radiation force balance calibrator 100 is mounted on a subject support 102. Below the subject support 102 is an ultrasound transducer system 104. The ultrasound transducer system 104 has a high intensity focused ultrasound transducer 106 within a fluid filled chamber 108. The fluid filled chamber 108 is located below the subject support 102. There is an ultrasound window 110 which allows ultrasound to leave the fluid filled chamber 108. The dashed lines marked 112 illustrate the path of ultrasound from the high intensity focused ultrasound transducer 106 through the ultrasound window 110 and into the radiation force balance calibrator 100. The path of the ultrasound radiation 112 is focused into a sonication zone 114. The sonication zone 114 is shown as being within an oil target phantom 116. The oil target phantom 116 is suspended in a bath of water 118. The water 118 is held by a basin 120. The basin 120 is fit such that it fits into the patient support 102 to cover the ultrasound window 110.

Above the basin 120 there is a balance 124. The oil target phantom 116 is connected to the balance 124 by small wires 126. The balance 124 has a first end 132 and a second end 134. The first end 132 has a pivot 128 which connects the balance 124 to a balance frame 130. The pivot 128 allows the balance 124 to pivot relative to the balance frame 130. The second end 134 of the balance 124 exerts force on a force sensor 138. The force sensor 138 is shown as having a force sensitive or measuring region 140 on which the second end 134 exerts force. The arrow 142 illustrates the direction of pivoting of the balance 124. The arrow labeled 144 indicates the direction of force applied by the second end 134 of the balance 124 on the force sensitive region 140.

Figure 2:
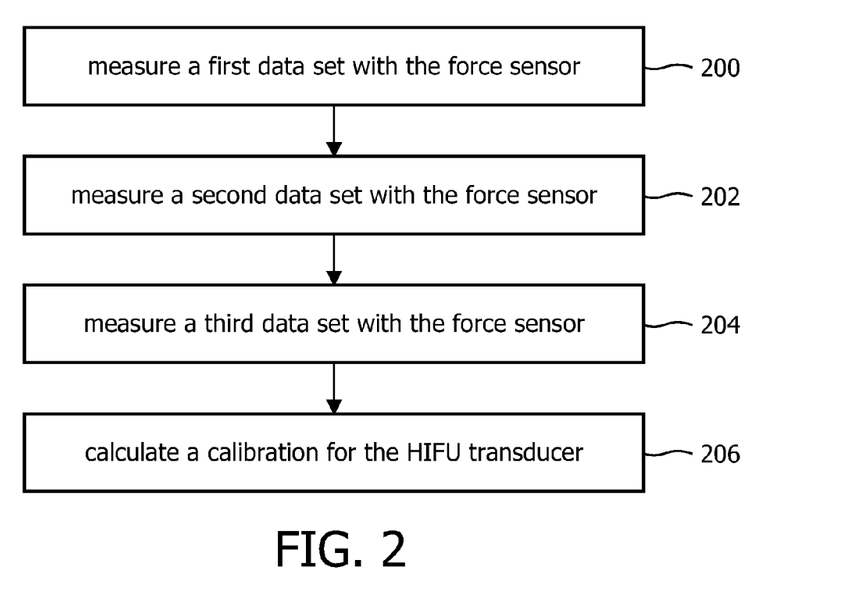
FIG. 2 shows a block diagraph which illustrates a method according to an embodiment of the invention.

FIG. 2 shows a flow diagram which illustrates a method according to an embodiment of the invention. In step 200 a first dataset is measured with the force sensor. At least a portion of the first dataset is acquired with a calibration weight in the calibration weight holder. In step 202 a second dataset is measured with the force sensor. A calibration weight is placed in the calibration weight holder when the second dataset is measured. Step 204 is measuring a third dataset with the force sensor. At least a portion of the third dataset is acquired with a calibration weight in the calibration weight holder. Finally in step 206 a calibration for the high intensity focused ultrasound transducer is calculated.

Figure 3:
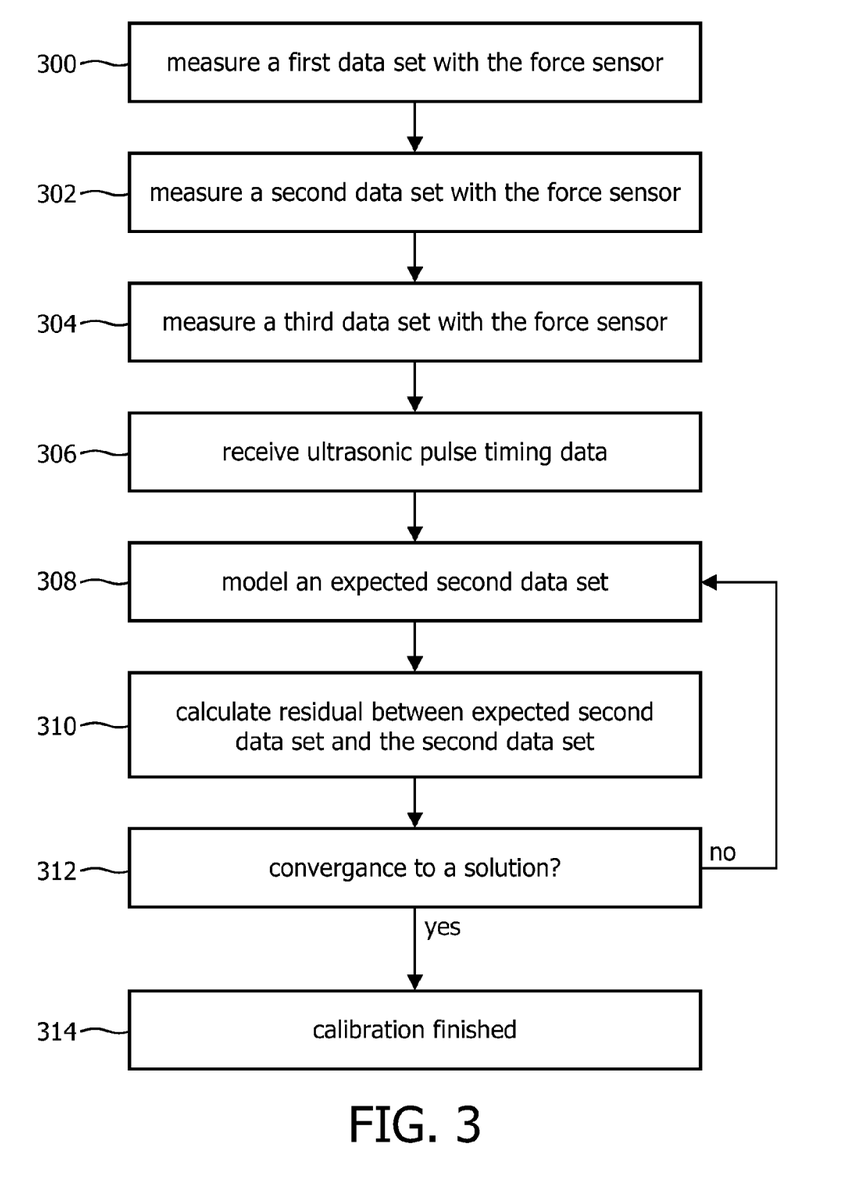
FIG. 3 shows a block diagraph which illustrates a method according to a further embodiment of the invention

FIG. 3 shows a flow diagram which illustrates a further method according to an embodiment of the invention. In step 300 a first dataset is measured with the force sensor. Step 300 corresponds to step 200 of FIG. 2. Step 302 is to measure a second dataset with the force sensor. Step 302 corresponds to step 202 of FIG. 2. In step 304 a third dataset is measured with the force sensor. Step 304 corresponds to step 204 of FIG. 2. Steps 306, 308, 310, 312 and 314 of FIG. 3 correspond to step 206 of FIG. 2. In step 306 ultrasonic pulse timing data is received. The ultrasonic pulse timing data is descriptive of the power of the ultrasonic radiation applied by the high intensity focused ultrasound transducer as a function of time. This is used in the calibration calculation.

In step 308 a model of an expected second dataset is calculated using the ultrasonic pulse timing data. In other words using the ultrasonic pulse timing data a simulated second dataset which is referred to here as an expected second dataset is calculated. Next in step 310 a residual is calculated between the expected second dataset and the second dataset which was measured. In step 312 convergence to a solution or a minimum threshold for the residual is checked. If the solution does not converge then the second dataset or the simulated or expected second dataset is recalculated and the method goes back to step 308. If the solution did converge then the calibration is finished in step 314.

Figure 4:
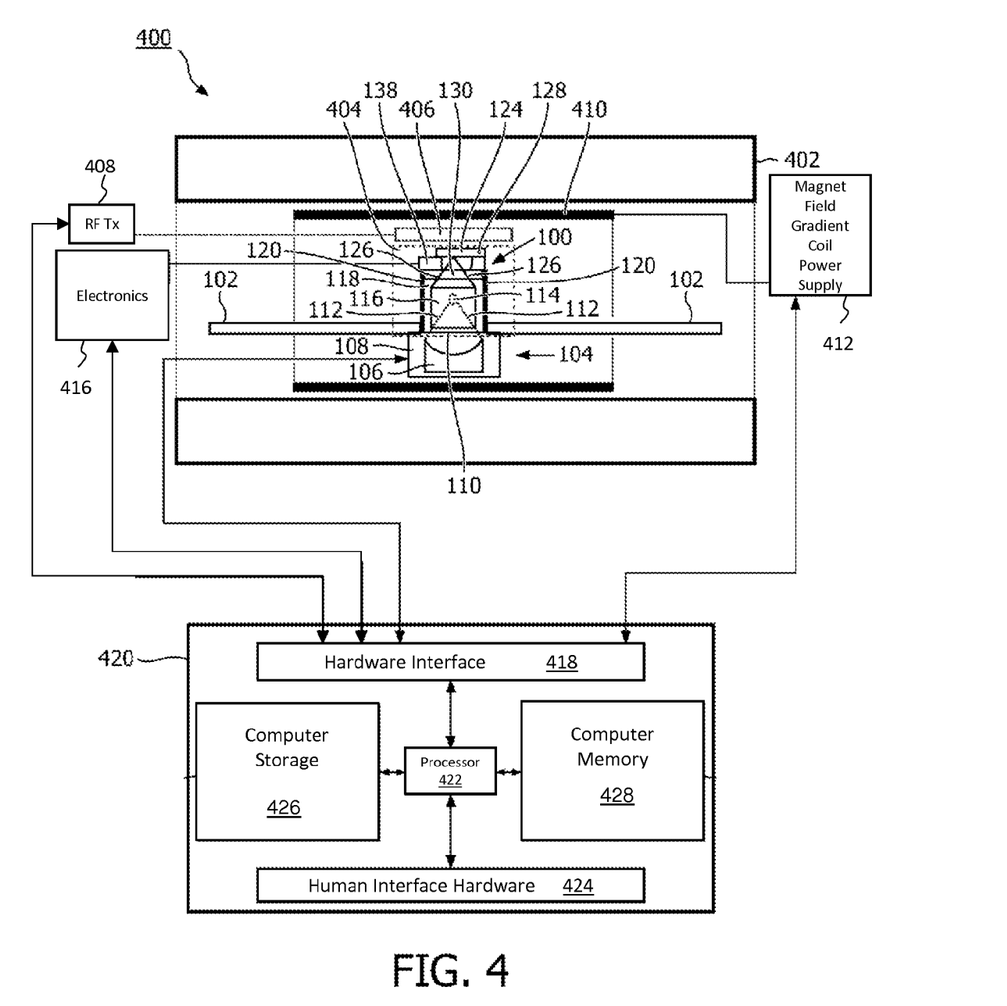
FIG. 4 shows a block diagram which illustrates an embodiment of an ultrasound apparatus according to the invention.

FIG. 4 shows a block diagram which illustrates an embodiment of an ultrasound apparatus 400 according to the invention. The ultrasound apparatus 400 comprises a magnetic resonance imaging system, a radiation force balance calibrator 100 and an ultrasound transducer system 104. The magnetic resonance imaging system comprises a magnet 402. The magnet 402 has an imaging zone 404 where the magnetic field is uniform enough for performing magnetic resonance imaging. The subject support 102, the ultrasound transducer system 104 and the radiation force balance calibrator 100 are all shown as being within the bore of the magnet 402. In many embodiments the subject support 102 is able to be removed from the magnet 402. In some embodiments the radiation force balance calibrator 100 is installed into the subject support 102 after the subject support 102 has been removed or partially removed from the magnet 402. Likewise in this figure not all details of the radiation force balance calibrator 100 that are shown in FIG. 1 are shown in this figure.

Above the imaging zone 404 is a radio frequency coil 406. The radio frequency coil is for acquiring magnetic resonance data from the imaging zone 404. The radio frequency coil 406 is connected to a radio frequency transceiver 408. Also within the bore of the magnet 410 is a magnetic field gradient coil. The magnetic field gradient coil 410 is connected to a magnet field gradient coil power supply 412. The magnetic field gradient coil power supply 412 supplies electrical current to the magnetic field gradient coil 410. Also shown is electronics 416 for the radiation force balance calibrator 100. Not shown in the diagram is a power supply and control electronics and possibly an actuator for the ultrasound transducer system 104.

The ultrasound transducer system 104, the radio frequency transceiver 408, the electronics 416 and the magnetic field gradient coil power supply 412 are all shown as being connected to a hardware interface 418 of a computer system 420. The computer system 420 further comprises a processor 422 which is connected to both the hardware interface 418 and a user interface 424. The hardware interface 418 comprises electronics which enable the processor 422 to send and receive messages to various pieces of hardware and for controlling them. The human interface hardware 424 comprises electronic and mechanical components which allow an operator to interact with the computer system 420. The human interface hardware 424 may comprise but is not limited to a keyboard, a mouse, and a display. The display of 424 may be used for operating graphical user interfaces for controlling the operation of the ultrasound apparatus 400 and also for displaying data or for rendering images such as magnetic resonance images. The processor 422 is also connected to computer storage 426 and computer memory 428.

Figure 4A:
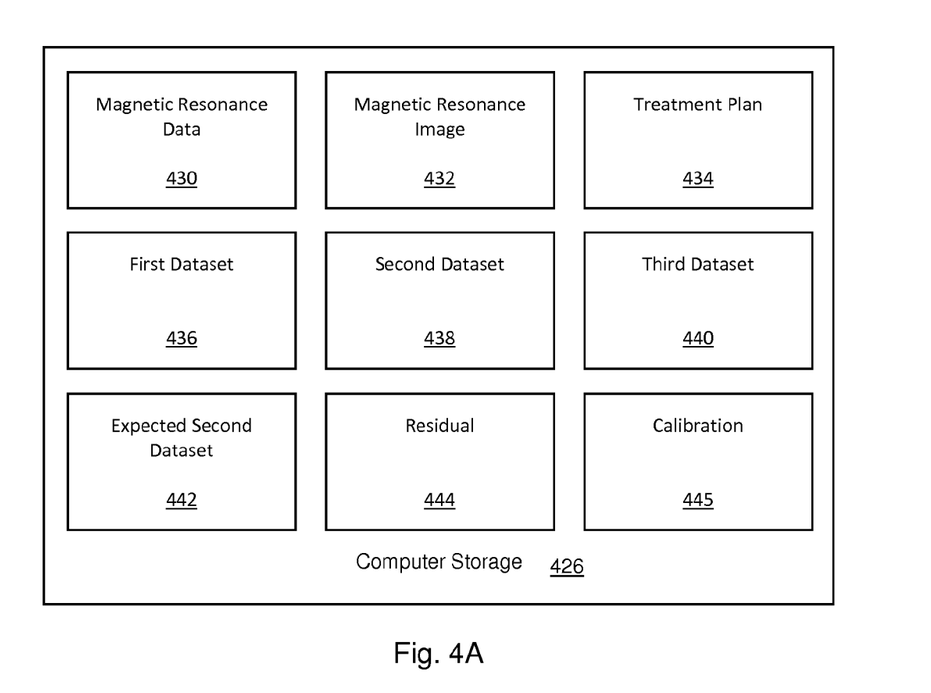
FIG. 4A illustrates modules incorporated within the computer storage illustrated by FIG. 4.

FIG. 4A illustrates modules incorporated within the computer storage illustrated by FIG. 4. The computer storage 426 is shown as containing magnetic resonance data 430 which has been acquired by the magnetic resonance imaging system. The computer storage is further shown as containing a magnetic resonance image 432 which has been reconstructed from the magnetic resonance data 430. Also within the computer storage 426 is stored a treatment plan 434 which contains instructions and/or control sequences for controlling the operation of the ultrasound transducer system 104 during the treatment of a subject. Also within the computer storage 426 is stored a first dataset 436. Also stored within the computer storage 426 is a second dataset 438. Also stored within the computer storage 426 is a third dataset 440. The first dataset 436, second dataset 438, and third dataset 440 were acquired during the course of calibrating the high intensity focused ultrasound transducer 106. Also stored within the computer storage 426 is an expected second dataset 442. Also stored within the computer storage 426 is a residual 444 between the second dataset 438 and the expected second dataset 442. Also stored within the computer storage 426 is a calibration 445 for the high intensity focused ultrasound transducer 106. The calibration 445 contains a mapping of electrical power delivered to the high intensity focused ultrasound transducer 106 to a power or intensity of ultrasonic radiation generated by the high intensity focused ultrasound transducer 106.

Figure 4B:
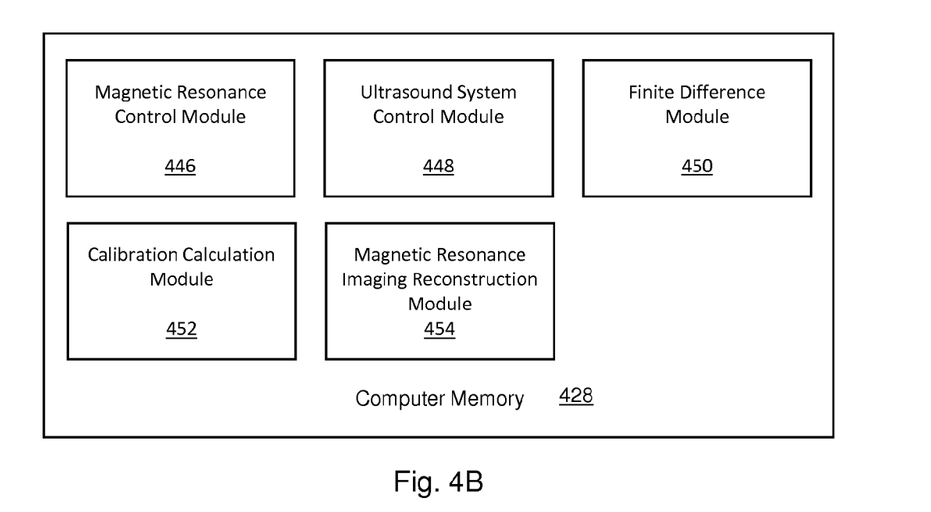
FIG. 4B illustrates modules incorporated within the computer memory illustrated by FIG. 4.

FIG. 4B illustrates modules incorporated within the computer memory illustrated by FIG. 4. Within the computer memory 428 there is a magnetic resonance control module 446. The magnetic resonance control module 446 contains computer executable code for controlling the operation and functioning of the magnetic resonance imaging system. Also within the computer memory 428 is an ultrasound system control module 448 which contains computer executable code for controlling the operation and functioning of the ultrasound transducer system 104. The ultrasound system control module 448 uses the treatment plan 434 to generate the control sequences for the ultrasound system. Also stored within the computer memory 428 is a finite difference module 450. The finite difference module 450 contains computer executable code for performing finite difference calculations. Also stored within the computer memory 428 is a calibration calculation module 452. The calibration calculation module 452 uses the finite difference module 450 and is able to calculate the calibration 445 using the first dataset 436, the second dataset 438, and the third dataset 440. The calibration calculation module 452 uses the finite difference module 450 for calculating the expected second dataset 442 and to calculate the residual 444. The calibration calculation module 452 may also contain computer executable code for automating the calibration procedure. The computer memory 428 is also shown as containing a magnetic resonance imaging reconstruction module 454. The magnetic resonance imaging reconstruction module 454 contains computer executable code for reconstructing the magnetic resonance image 432 from the magnetic resonance data 430.

Figure 5A:
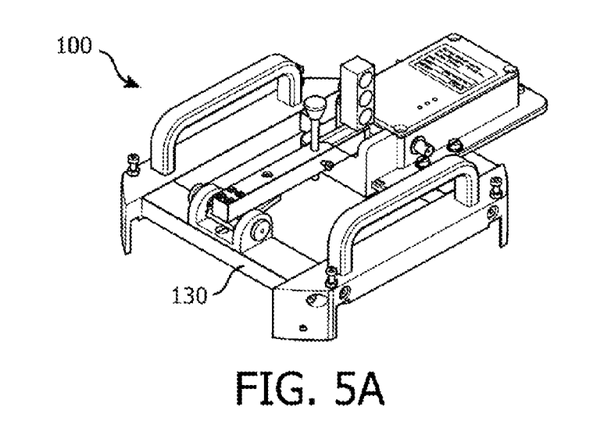
FIG. 5a shows an isometric view of a radiation force balance calibrator according to an embodiment of the invention.
Figure 5B:
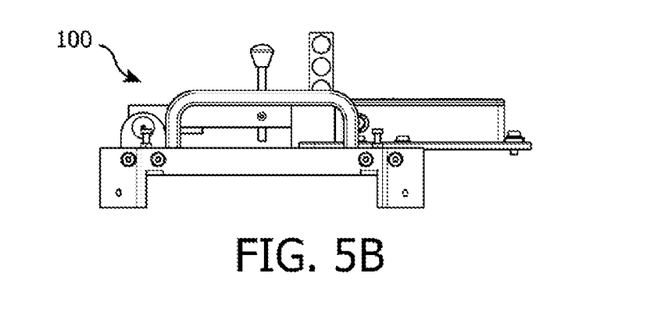
Figure 5C:
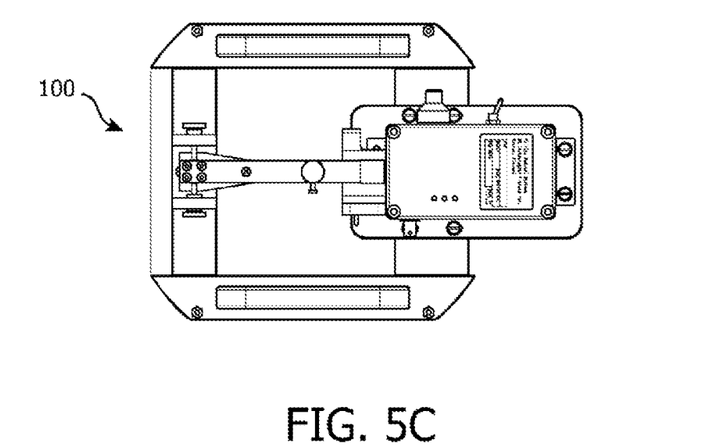
Figure 5D:
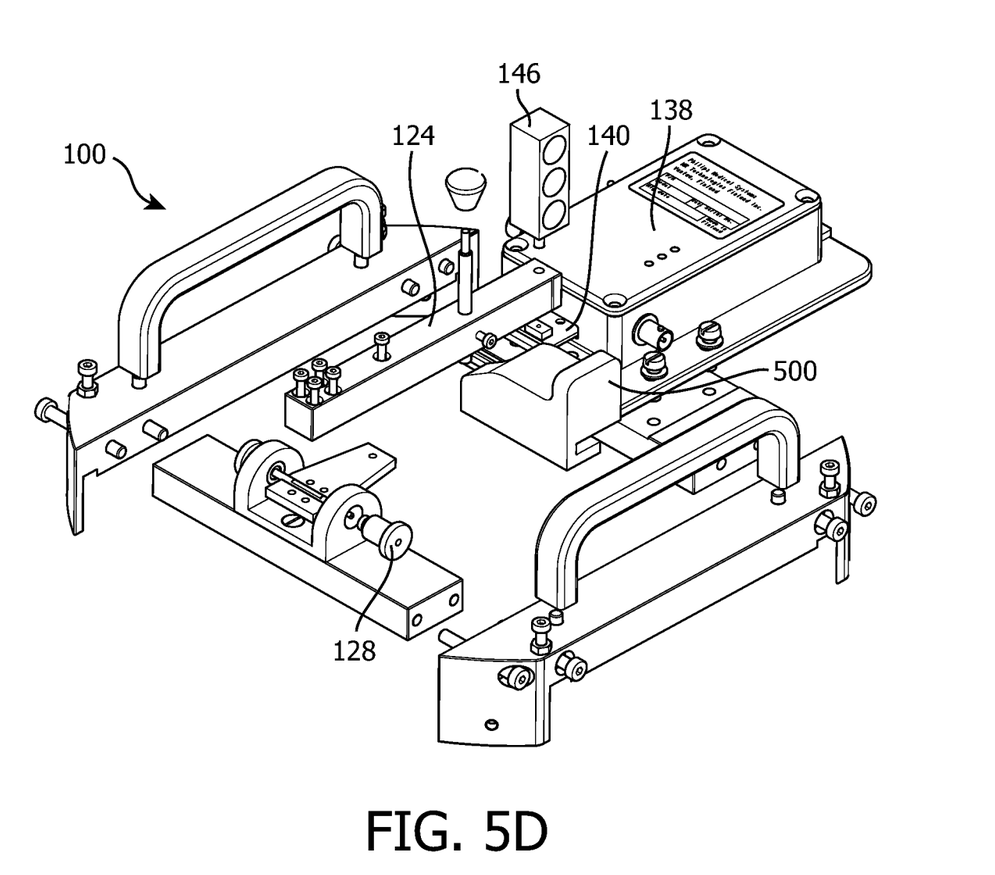
FIG. 5d shows an exploded parts view of the radiation force balance calibrator shown in FIG. 5d.

FIGS. 5a, 5b, 5c, and 5d show different views of an embodiment of a radiation force balance calibrator according to the invention. FIG. 5a shows an isometric view, FIG. 5b shows a side view, FIG. 5c shows a top view, and FIG. 5d shows an exploded isometric view. Shown in these figures is arrestor block 500. The arrestor block 500 can be used to prevent the balance 124 from contacting the force sensitive region 140 when the radiation force balance calibrator 100 is not in use.

Figure 6A:
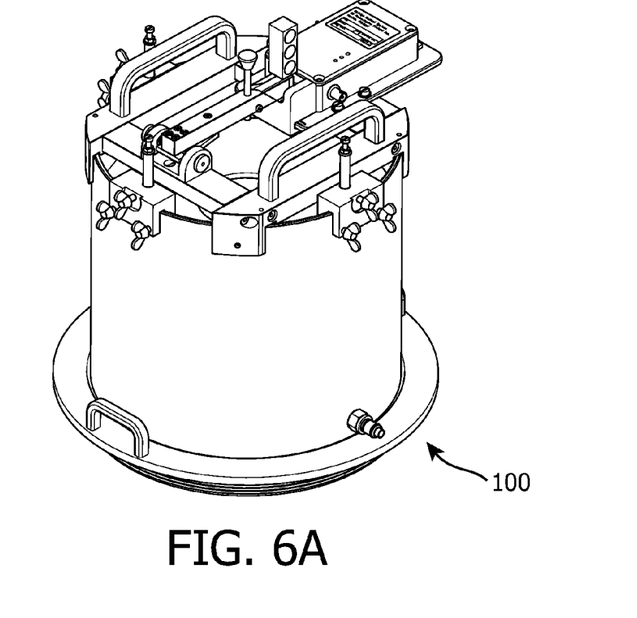
FIG. 6a shows an isometric view the radiation force balance calibrator of FIG. 5a assembled with a basin.
Figure 6B:
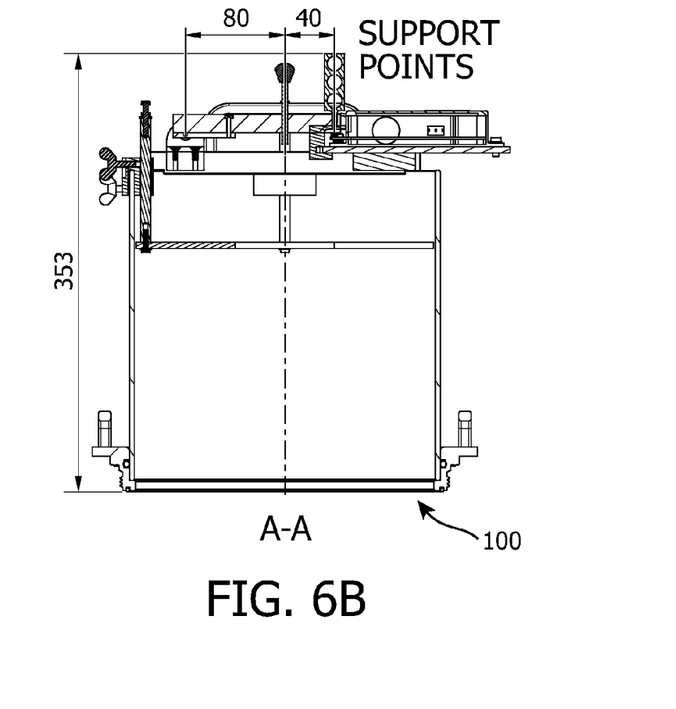
Figure 6C:
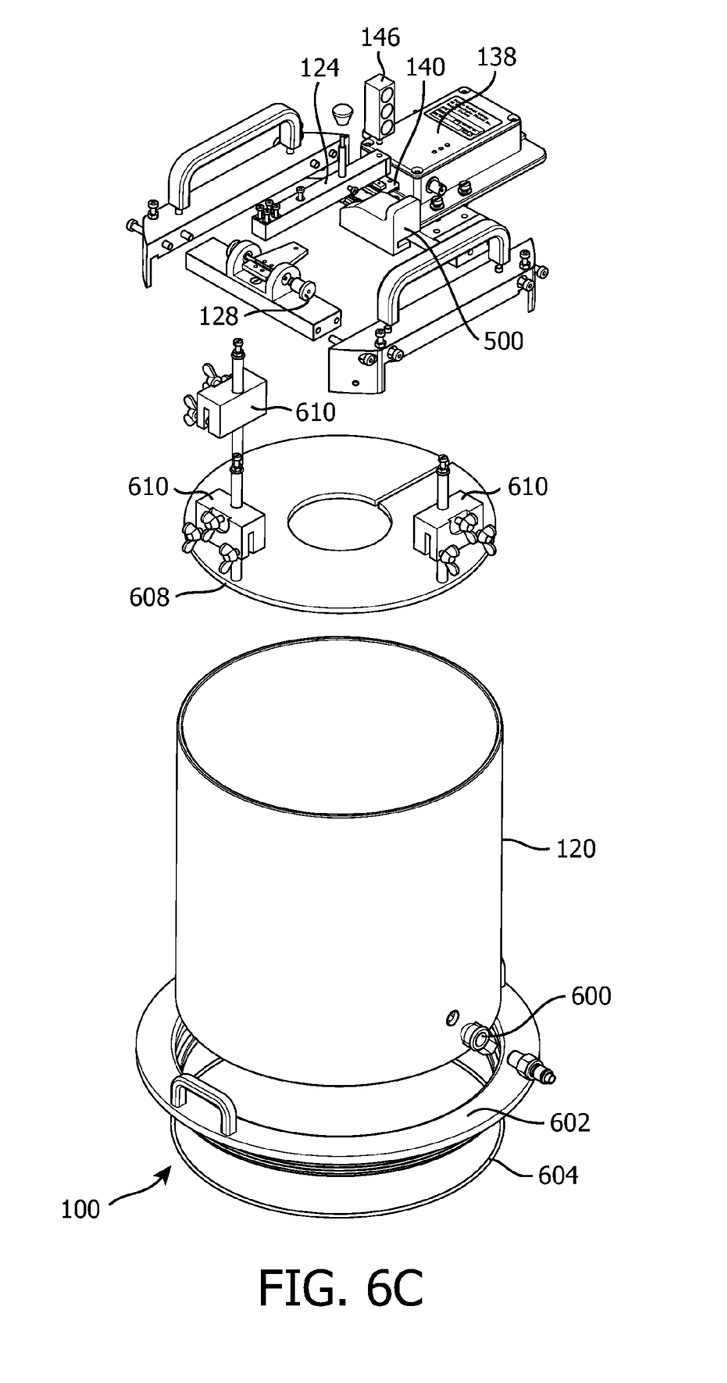
Figure 7:
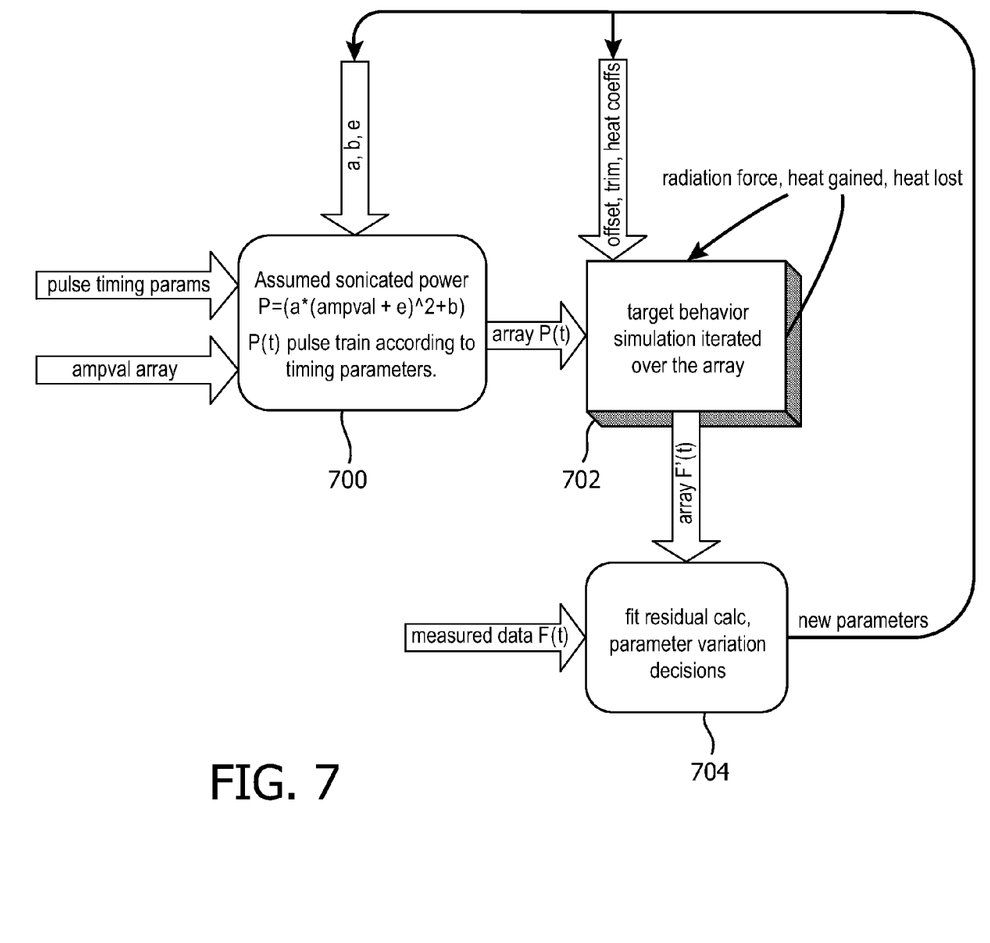
FIG. 7 shows a method according to a further embodiment of the invention.

FIGS. 6a, 6b, and 6c show drawings which illustrate the same radiation force balance calibrator 100 mounted onto a basin 120 for connecting to a subject support. FIG. 6a shows an isometric view, FIG. 6b shows a cut-away or cross-sectional side view, and FIG. 6c shows an exploded part view in isometric. Connected to the basin is a drain plug 600. The basin 120 is shown as fitting into an adaptor 602 which allows installation of the radiation force balance calibrator 100 into a subject support over an ultrasonic window. Between the oil target phantom and the balance frame 130 there is a plate 608. The plate is adjusted such that the plate is exactly at the height of the water filling the basin 120. The plate stabilizes the water and reduces vibrations during measurement. The plate 608 is suspended or held on the basin 120 by clamps 610. One embodiment of a method for performing a calibration using the apparatus of FIGS. 5 and 6 is:

1. Record the first data set
   a. Remove all the calibration weights.
   b. Remove all personnel from the vicinity of the bed and let the system settle for a minute. Record about 20 seconds of data and pause recording.
   c. Insert the 10 g weight in the bottom slot of the weight cage.
   d. Repeat 1.b
   e. Insert the 5 g weight in the middle slot of the weight cage.
   f. Repeat 1.b
   g. Insert the 2 g weight in the top slot of the weight cage.
   h. Repeat 1.b
2. Perform a sonication with the ultrasound transducer and record the second data set.
   a. Start recording data from the force sensor
   b. Start the sonication protocol. The protocol will run to completion or it can stop with an error, typically when reaching the highest power levels. If this happens, make a note of the error message and include a description of the comments.
   c. Pause the recording of data from the force sensor.
3. Record the third dataset
   a. Let the system cool down from the sonications for about 5 minutes, this will mitigate the effects of the buoyancy drift. (Some drift is inevitable and acceptable, this data serves as only a rough check of integrity after sonication).
   b. Record about 20 seconds of data and pause recording.
   c. Remove the 2 g weight from the top slot of the weight cage.
   d. Remove all personnel from the vicinity of the bed and let the system settle for a minute.
   Record about 20 seconds of data and pause recording.
   e. Remove the 5 g weight from the middle slot of the weight cage.
   f. Repeat 3.d
   g. Remove the 10 g weight from the bottom slot of the weight cage.
   h. Repeat 3.d FIG. 7 illustrates a method of performing a calibration with a radiation force balance calibrator according to the invention. The method simulates the Radiation Force Balance (RFB) target behavior over the measurement trace To withstand data which is noisy or distorted by large buoyancy effects. In step 700, every iteration first produces an array of electrical power values according to $P=a*(ampval+e)2+b$ where a, b and e are fit parameters.

Then this assumed electrical power (as function of time) is fed to a difference equation module 702, which takes in fit parameters for heat gain and loss as well as parameters to account for non-equilibrium buoyancy. The module outputs an array of assumed balance indicated weight readings, which goes to Levenberg-Marquardt nonlinear least squares minimization algorithm. In step 704, a residual is calculated between the simulated and the measured data. If convergence to a solution is not achieved, the algorithm varies the fit parameters and starts the next iteration round.

This is contrasted with the traditional way of taking generator reported power as the fit target data and fitting a function in the form $P=a*(ampval+e)2+b$ to it. This formula is used to predict electrical power, and acoustic power is then obtained by multiplying with a constant $W_{el}$ to $W_{ac}$. The main difference of these methods is the fit target: the traditional way fits to reported generator power, the new method fits to a balance acoustic power trace.

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein the calibration weights are automatically added to or removed from the calibration weight holder. For instance a robotic system may be used to accomplish this.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS

100 radiation force balance calibrator
102 subject support
104 ultrasound transducer system 106 high intensity focused ultrasound transducer
108 fluid filled chamber
110 ultrasound window
112 path of ultrasound
114 sonication zone
116 oil target phantom
118 water
120 basin
124 balance
126 wire
128 pivot
130 balance frame
132 first end
134 second end
138 force sensor
140 force sensitive region
142 direction of pivoting
144 direction of force
146 calibration weight holder
400 ultrasound apparatus
402 magnet
404 imaging zone
406 radio frequency coil
408 radio frequency transceiver
410 magnetic field gradient coil
412 magnetic field gradient coil power supply
416 radiation force balance calibrator electronics
418 hardware interface
420 computer system
422 processor
424 human interface hardware
426 computer storage
428 computer memory
430 magnetic resonance data
432 magnetic resonance image
434 treatment plan
436 first data set
438 second data set
440 third data set
442 expected second data set
444 residual
445 calibration
446 magnetic resonance control module
448 ultrasound system control module
450 finite difference module
452 calibration calculation module
454 magnetic resonance image reconstruction module
500 arrestor block
600 drain plug
602 adaptor
604 O-ring
608 plate
610 clamps

The invention claimed is:

1. A radiation force balance calibrator for calibrating a high intensity focused ultrasound transducer, the radiation force balance calibrator comprising:
a balance frame;
a force sensor for measuring force, wherein the force sensor is attached to the balance frame;
a balance having a first end and a second end, wherein the first end is attached to a pivot for enabling the balance to pivot relative to the balance frame, wherein the second end is adapted for exerting force onto the force sensor;
a calibration weight holder attached to the second end; and
an oil target phantom connected to the balance for absorbing ultrasound radiation from the high intensity focused ultrasound transducer, wherein the absorption of ultrasonic radiation causes a reduction in the force exerted by the balance on the force sensor;
wherein the radiation force balance calibrator is constructed of non-magnetic materials, and further comprises a processor and a memory, the memory comprising instructions for execution by the processor, wherein execution of the instructions causes the processor to perform:
computing an estimated force on the oil target phantom due to absorbing the ultrasound radiation from the high intensity focused ultrasound transducer on a basis of activation signals to activate the high intensity focused ultrasound transducer to emit the ultrasound radiation and model parameters that are descriptive for a relationship between the activation signals and the output power of the high intensity focused ultrasound transducer and a transfer of the output power to the force exerted by the balance on the force sensor,
ii. activate the high intensity focused ultrasound transducer and measure the force exerted by the balance on the force sensor,
iii. compute a difference between a measured force and the estimated force, and
iv. update the model parameters on a basis of the computed difference and iterate i. through iv. until the computed difference is less than a pre-determined threshold.

2. The radiation force balance calibrator of claim 1, wherein the execution of the instructions further causes the processor to perform:
measuring a first data set with the force sensor, wherein at least a portion of the first data set is acquired with a calibration weight in the calibration weight holder;
measuring a second data set representing the force exerted by the balance on the force sensor, with the force sensor having a calibration weight in the calibration weight holder, wherein the second data set is measured after the first data set, wherein at least some of the second data set is measured when the oil target phantom is absorbing the ultrasonic radiation;
measuring a third data set with the force sensor, wherein at least a portion of the third data set is acquired with a calibration weight in the calibration weight holder, wherein the third data set is measured after the second data set; and
calculating a calibration for the high intensity focused ultrasound transducer using the first data set, the second data set, and the third data set.

3. The radiation force balance calibrator of claim 2, wherein at least some of the second set of data is measured when the oil target phantom is absorbing ultrasonic radiation of at least two different intensities, wherein the instructions further cause the processor to perform a receiving the activation signals in a form of ultrasonic pulse timing data descriptive of ultrasonic radiation emitted by the high intensity focused ultrasound transducer during the measurement of the second data set, wherein the calibration is calculated using the ultrasonic pulse timing data.

4. The radiation force balance calibrator of claim 3, wherein the calculating the calibration comprises:
modeling an expected second data set, corresponding to the estimated force on the oil target phantom using the ultrasonic pulse timing data, wherein the ultrasonic pulse timing data is descriptive of an intended intensity of ultrasonic radiation; and calculating the difference between the measured force and the estimated force as a residual between the expected second data set and the second data set;

wherein the modeling and the calculation of the residual are repeated iteratively until the model converges to the calibration.

5. The radiation force balance calibrator of claim 4, wherein the modeling is performed using a finite difference model for simulating radiation force of ultrasonic radiation on the oil target phantom.

6. The radiation force balance calibrator of claim 5, wherein the finite difference model is adapted for simulating the buoyancy of the oil target phantom by calculating heat transfer due to the absorption of the ultrasonic radiation within the oil target phantom and heat exchange with its surroundings.

7. The radiation force balance calibrator of claim 1, wherein the functioning of the force sensor is not affected by a magnetic field with a strength under 20 Tesla.

8. The radiation force balance calibrator of claim 1, wherein the force sensor is a micro-machined silicon bridge sensor.

9. An ultrasound apparatus comprising:
a patient support;
an ultrasound transducer system, the ultrasound transducer system being mounted below an ultrasound window in the patient support, the ultrasound apparatus comprising a radiation force balance calibrator, comprising:
a balance frame;
a force sensor for measuring force, wherein the force sensor is attached to the balance frame;
a balance with different first and second ends, wherein the first end is attached to a pivot for enabling the balance to pivot relative to the balance frame, wherein the second end is adapted for exerting force onto the force sensor;
a calibration weight holder attached to the second end; and
an oil target phantom connected to the balance for absorbing ultrasound radiation from the high intensity focused ultrasound transducer, wherein the absorption of ultrasonic radiation causes a reduction in the force exerted by the balance on the force sensor; wherein the radiation force balance calibrator is constructed of non-magnetic materials, and further comprises a processor and a memory, the memory comprising instructions for execution by the processor, wherein execution of the instructions causes the processor to perform:
  i. computing an estimated force on the oil target phantom due to absorbing the ultrasound radiation from the high intensity focused ultrasound transducer on a basis of activation signals to activate the high intensity focused ultrasound transducer to emit the ultrasound radiation and model parameters that are descriptive for a relationship between the activation signals and the output power of the high intensity focused ultrasound transducer and a transfer of the output power to the force exerted by the balance on the force sensor,
  ii. activate the high intensity focused ultrasound transducer and measure the force exerted by the balance on the force sensor,
  iii. compute a difference between a measured force and the estimated force, and
  iv. update the model parameters on a basis of the computed difference and iterate i. through iv. until the computed difference is less than a pre-determined threshold, wherein the radiation force balance calibrator is mounted above the ultrasound window.

10. The ultrasound apparatus of claim 9, wherein the ultrasound apparatus further comprises a magnetic resonance imaging system, wherein the magnetic resonance imaging system comprising:
a magnet adapted for generating a magnetic field for orientating the magnetic spins of nuclei of a subject located within an imaging volume;
a radio frequency transceiver, wherein the radio frequency transceiver is adapted for connecting to a radio frequency coil for acquiring magnetic resonance data from the imaging volume;
a magnetic field gradient coil for spatial encoding of the magnetic spins of nuclei within the imaging volume;
a magnetic field gradient coil power supply for supplying current to the magnetic field gradient coil; and
a computer system for controlling the operation of the magnetic resonance imaging system and the ultrasound transducer system, wherein the computer system is adapted for controlling the ultrasound transducer system using the magnetic resonance data.

11. The ultra sound apparatus of claim 9, wherein the execution of the instructions further causes the processor to perform:
measuring a first data set with the force sensor, wherein at least a portion of the first data set is acquired with a calibration weight in the calibration weight holder;
measuring a second data set representing the force exerted by the balance on the force sensor, with the force sensor having a calibration weight in the calibration weight holder, wherein the second data set is measured after the first data set, wherein at least some of the second data set is measured when the oil target phantom is absorbing the ultrasonic radiation;
measuring a third data set with the force sensor, wherein at least a portion of the third data set is acquired with a calibration weight in the calibration weight holder, wherein the third data set is measured after the second data set; and
calculating a calibration for the high intensity focused ultrasound transducer using the first data set, the second data set, and the third data set.

12. The ultrasound apparatus of claim 11, wherein at least some of the second set of data is measured when the oil target phantom is absorbing ultrasonic radiation of at least two different intensities, wherein the instructions further cause the processor to perform a receiving the activation signals in a form of ultrasonic pulse timing data descriptive of ultrasonic radiation emitted by the high intensity focused ultrasound transducer during the measurement of the second data set, wherein the calibration is calculated using the ultrasonic pulse timing data.

13. The ultrasound apparatus of claim 12, wherein the calculating the calibration comprises:
modeling an expected second data set, corresponding to the estimated force on the oil target phantom using the ultrasonic pulse timing data, wherein the ultrasonic pulse timing data is descriptive of an intended intensity of ultrasonic radiation; and
calculating the difference between the measured force and the estimated force as a residual between the expected second data set and the second data set;
wherein the modeling and the calculation of the residual are repeated iteratively until the model converges to the calibration.

14. The ultrasound apparatus of claim 13, wherein the modeling is performed using a finite difference model for simulating radiation force of ultrasonic radiation on the oil target phantom.

15. The ultrasound apparatus of claim 14, wherein the finite difference model is adapted for simulating the buoyancy of the oil target phantom by calculating heat transfer due to the absorption of the ultrasonic radiation within the oil target phantom and heat exchange with its surroundings.

16. The ultrasound apparatus of claim 9, wherein the functioning of the force sensor is not affected by a magnetic field with a strength under 20 Tesla.

17. The ultrasound apparatus of claim 9, wherein the force sensor is a micro-machined silicon bridge sensor.

18. A non-transitory computer readable storage medium comprising machine executable instructions for execution by a processor of a radiation force balance calibrator, the radiation force balance calibrator comprising: a balance frame; a force sensor for measuring force, wherein the force sensor is attached to the balance frame; a balance with different first and second ends, wherein the first end is attached to a pivot for enabling the balance to pivot relative to the balance frame, wherein the second end is adapted for exerting force onto the force sensor; a calibration weight holder attached to the second end; an oil target phantom connected to the balance for absorbing ultrasound radiation from a high intensity focused ultrasound transducer, wherein the absorption of ultrasonic radiation causes a reduction in the force exerted by the balance on the force sensor, wherein execution of the instructions causes the processor to perform:
  i. computing an estimated force on the oil target phantom due to absorbing the ultrasound radiation from the high intensity focused ultrasound transducer on a basis of activation signals to activate the high intensity focused ultrasound transducer to emit the ultrasound radiation and model parameters that are descriptive for a relationship between the activation signals and the output power of the transducer and a transfer of the output power to the force exerted by the balance on the force sensor,
  ii. activate the high intensity focused ultrasound transducer and measure the force exerted by the balance on the force sensor,
  iii. compute a difference between the measured force and the estimated force, and
  iv. update the model parameters on a basis of the computed difference and iterate i. through iv. until the computed difference is less than a pre-determined threshold.

19. The non-transitory computer-readable storage medium of claim 18, wherein execution of the instructions further causes the processor to perform:
  measuring a first data set with the force sensor, wherein at least a portion of the first data set is acquired with a calibration weight in the calibration weight holder;
  measuring a second data set with the force sensor with a calibration weight in the calibration weight holder, wherein the second data set is measured after the first data set, wherein the second set of data is measured when the oil target phantom is absorbing the ultrasonic radiation;
  measuring a third data set with the force sensor, wherein at least a portion of the third data set is acquired with a calibration weight in the calibration weight holder, wherein the third data set is measured after the second data set; and
  calculating a calibration for the high intensity focused ultrasound transducer using the first data set, the second data set, and the third data set.

20. A computer-implemented method of calibrating a high intensity focused ultrasound transducer using a radiation force balance calibrator, the radiation balance calibrator comprising: a balance frame; a force sensor for measuring force, wherein the force sensor is attached to the balance frame; a balance with different first and second ends, wherein the first end is attached to a pivot for enabling the balance to pivot relative to the balance frame, wherein the second end is adapted for exerting force onto the force sensor; a calibration weight holder attached to the second end; an oil target phantom connected to the balance for absorbing ultrasound radiation from the high intensity focused ultrasound transducer, wherein the absorption of the ultrasonic radiation causes a reduction in the force exerted by the balance on the force sensor, the method comprising:
  measuring a first data set with the force sensor, wherein at least a portion of the first data set is acquired with a calibration weight in the calibration weight holder;
  measuring a second data set with the force sensor with a calibration weight in the calibration weight holder, wherein the second data set is measured after the first data set, wherein the second data set is measured when the oil target phantom is absorbing the ultrasonic radiation;
  measuring a third data set with the force sensor, wherein at least a portion of the third data set is acquired with a calibration weight in the calibration weight holder, wherein the third data set is measured after the second data set; and
  calculating a calibration for the high intensity focused ultrasound transducer using the first data set, the second data set, and the third data set.

* * * * *